(12) United States Patent
Taki et al.

(10) Patent No.: US 9,978,044 B2
(45) Date of Patent: May 22, 2018

(54) ANALYZING DEVICE

(75) Inventors: Miki Taki, Hitachinaka (JP); Naomi Ishii, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 780 days.

(21) Appl. No.: 13/980,909

(22) PCT Filed: Jan. 10, 2012

(86) PCT No.: PCT/JP2012/000068
§ 371 (c)(1),
(2), (4) Date: Jul. 22, 2013

(87) PCT Pub. No.: WO2012/120755
PCT Pub. Date: Sep. 13, 2012

(65) Prior Publication Data
US 2013/0311243 A1  Nov. 21, 2013

(30) Foreign Application Priority Data

Mar. 4, 2011 (JP) ................................. 2011-047076

(51) Int. Cl.
  G06Q 10/00 (2012.01)
  G01N 35/00 (2006.01)
  G06Q 10/06 (2012.01)
(52) U.S. Cl.
  CPC ......... *G06Q 10/20* (2013.01); *G01N 35/0092* (2013.01); *G01N 35/00623* (2013.01); *G06Q 10/0639* (2013.01)
(58) Field of Classification Search
  None
  See application file for complete search history.

(56) References Cited

U.S. PATENT DOCUMENTS 4,512,442 A * 4/1985 Moore .................. B66B 5/0006
  187/393
5,100,622 A * 3/1992 Mimura ........... G01N 35/00594
  356/73
(Continued)

FOREIGN PATENT DOCUMENTS

EP  0359049 B1 * 11/1994 ....... G01N 35/00712
EP  0387787 B1 *  6/1997 ....... G01N 35/00594
(Continued)

OTHER PUBLICATIONS

Patterson, Wayne, et al. "Random and continuous-access immunoassays with chemiluminescent detection by Access automated analyzer." Clinical chemistry 40.11 (1994): 2042-2045.*
(Continued)

*Primary Examiner* — Thomas L Mansfield
*Assistant Examiner* — Derick Holzmacher
(74) *Attorney, Agent, or Firm* — Mattingly & Malur, PC

(57) ABSTRACT

An analyzing device requires regular maintenance for maintaining a predetermined analyzing performance thereof. However, the more complex the analyzing device becomes, the more number of maintenance items are provided. For example, if a plurality of types of maintenances to be performed by removing same component, efficiency may be improved by performing the same as a whole. However, when conforming with a manual, if recommended timings to perform the maintenance are shifted delicately, there is a probability of occurrence of a case where the same components are removed several times for maintenance during a short time. At the time when an instruction to perform maintenance is issued, maintenance items to be performed are extracted, the extracted maintenance items are sorted into a recommended performance order in conformity to a preset rule such that the similar maintenance or the main- (Continued)

tenance of the same portion or the like are performed continuously.

12 Claims, 14 Drawing Sheets

(56) References Cited

U.S. PATENT DOCUMENTS

| | | | | |
|---|---|---|---|---|
| 5,695,718 A * | 12/1997 | Imai | | G01N 35/00594 340/521 |
| 5,705,977 A * | 1/1998 | Jones | | B60Q 9/00 340/438 |
| 6,522,976 B2 * | 2/2003 | Shiba | | G01N 35/00584 422/63 |
| 7,384,601 B2 * | 6/2008 | Matsubara | | G01N 35/00712 422/62 |
| 7,769,565 B2 * | 8/2010 | Fujita | | G01N 35/00722 702/187 |
| 8,040,757 B2 * | 10/2011 | Wakamiya | | G01N 35/00663 368/10 |
| 8,131,382 B2 * | 3/2012 | Asada | | G01N 35/00871 700/3 |
| 8,709,345 B2 * | 4/2014 | Adachi | | G01N 35/025 356/246 |
| 2004/0102997 A1 * | 5/2004 | Kikuchi | | G01N 35/00663 422/62 |
| 2004/0161851 A1 * | 8/2004 | Horimoto | | G01N 35/00603 436/63 |
| 2005/0175506 A1 * | 8/2005 | Matsubara | | G01N 35/00712 422/68.1 |
| 2006/0190195 A1 * | 8/2006 | Watanabe | | G01N 35/00594 702/32 |
| 2007/0279653 A1 | 12/2007 | Bonikowski | | |
| 2008/0050280 A1 * | 2/2008 | Fujita | | G01N 35/00584 422/67 |
| 2013/0138472 A1 * | 5/2013 | Hasegawa | | G06Q 10/20 705/7.26 |

FOREIGN PATENT DOCUMENTS

| | | | | |
|---|---|---|---|---|
| EP | 0387787 B1 * | 6/1997 | | G01N 35/00594 |
| EP | 0871034 A2 * | 10/1998 | | G01N 35/00712 |
| EP | 1413888 A1 * | 4/2004 | | G01N 35/00603 |
| EP | 1413888 A1 * | 4/2004 | | G01N 35/00603 |
| EP | 1600779 A2 * | 11/2005 | | G01N 35/00594 |
| EP | 0732591 B1 * | 9/2006 | | G01N 35/00663 |
| EP | 2042875 A2 * | 4/2009 | | G01N 35/00871 |
| EP | 2042875 A3 * | 3/2015 | | G01N 35/00871 |
| EP | 2919015 A1 * | 9/2015 | | G01N 35/00623 |
| EP | 2919015 A1 * | 9/2015 | | G01N 35/00623 |
| JP | 01-305337 A | 12/1989 | | |
| JP | 03-148068 A | 6/1991 | | |
| JP | 06026025 A * | 2/1994 | | |
| JP | 08-304581 A | 11/1996 | | |
| JP | 2002-162400 A | 6/2002 | | |
| JP | 2007010233 A * | 1/2007 | | |
| JP | 2007-068721 A | 3/2007 | | |
| JP | 2007-323643 A | 12/2007 | | |
| JP | 2008-051532 A | 3/2008 | | |
| JP | 2008-051542 A | 3/2008 | | |
| JP | 2010-249757 A | 11/2010 | | |
| WO | WO-2014073684 A1 * | 5/2014 | | G01N 35/00623 |
| WO | WO-2015179300 A1 * | 11/2015 | | A61M 16/0463 |

OTHER PUBLICATIONS

Glasser, L. G. "Automatic photoelectric ultraviolet analyzer for continuous chemical analysis of process streams." JOSA 45.7 (1955): 556-563.*

Rausand, Marvin. "Reliability centered maintenance." Reliability Engineering & System Safety 60.2 (1998): 121-132.*

Rausand, Marvin. "Reliability centered maintenance." Reliability Engineering & System Safety 60.2 (1998): 121-132. (Year: 1998).*

Patterson, Wayne, et al. "Random and continuous-access immunoassays with chemiluminescent detection by Access automated analyzer." Clinical chemistry 40.11 (1994): 2042-2045. (Year: 1994).*

FitzGerald, Stephen P., et al. "Development of a high-throughput automated analyzer using biochip array technology." Clinical chemistry 51.7 (2005): 1165-1176. (Year: 2005).*

Broughton, P. M. G., et al. "A revised scheme for the evaluation of automatic instruments for use in clinical chemistry." Annals of Clinical Biochemistry 11.1-6 (1974): 207-218. (Year: 1974).*

* cited by examiner

[Fig. 1]
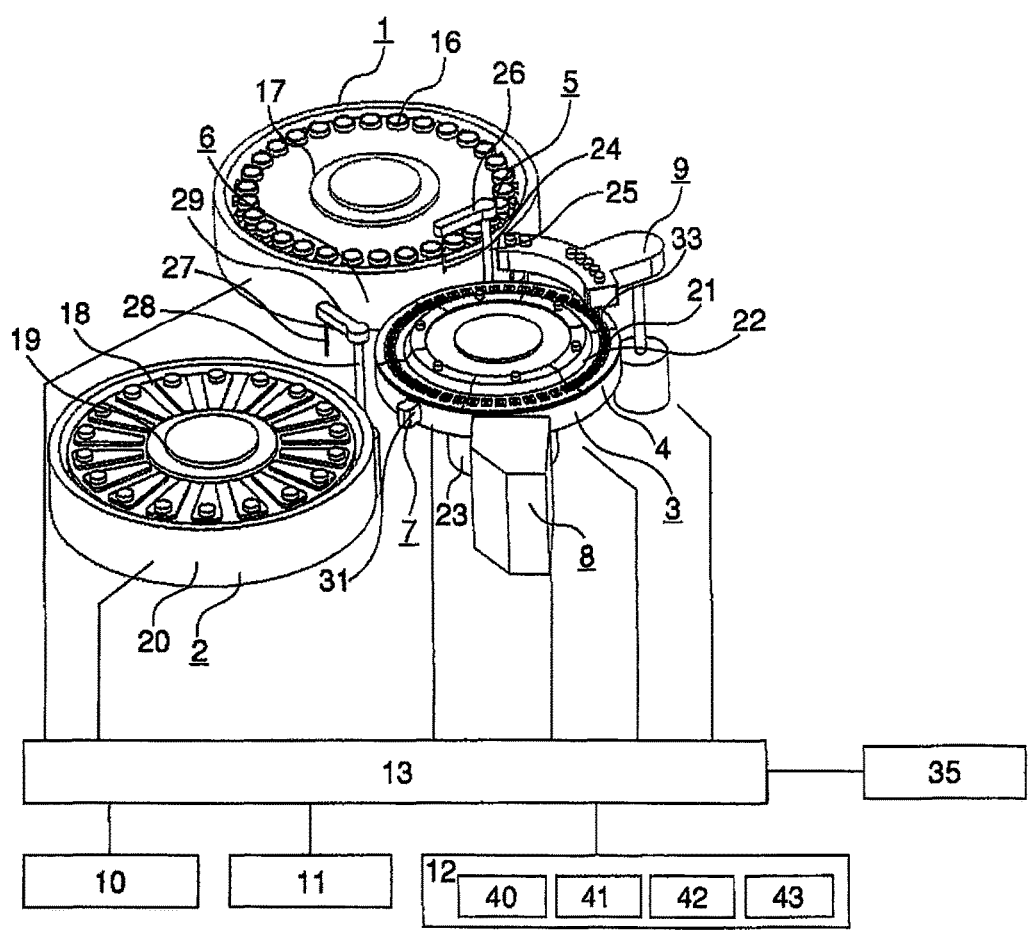

[Fig. 2]
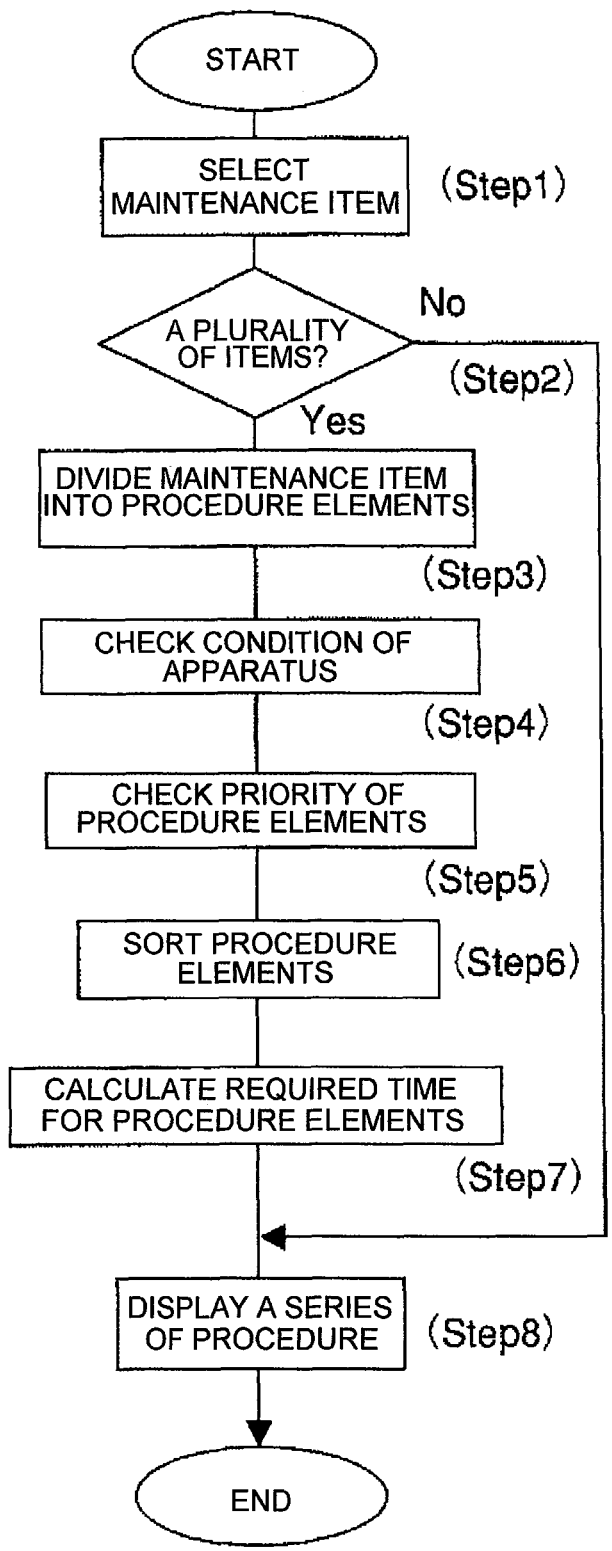

[Fig. 3a]

| WEEKLY | EVERY MONTH | EVERY THREE MONTHS |
|---|---|---|
| ☑ REACTING PARTS WASHING | ☑ REACTION CELL REPLACEMENT | ☐ ULTRASONIC MIXING AND IRRADIATED SURFACE CLEANING |
| ☑ CELL COVER CLEANING | ☑ REACTION TANK CLEANING | ☐ WATER SUPPLY FILTER CLEANING |
| ☑ WASHING TANK CLEANING | ☐ HEAT RADIATOR FILTER CLEANING | ☐ PIPETTER SEAL PIECE REPLACEMENT |
| ☑ WATER SUPPLY TANK CLEANING | ☑ BIFURCATED TUBE FILTER CLEANING | ☐ SUCTION TUBE REPLACEMENT |

[Fig. 3b]

| EVERY WEEK | EVERY MONTH | EVERY TWO MONTHS |
|---|---|---|
| ☑ WASHING TANK CLEANING<br>☐ CELL COVER CLEANING<br>☐ WASHING TANK CLEANING<br>☐ WATER SUPPLY TANK CLEANING | ☑ ISE REAGENT FLOW PATH WASHING<br>☑ REAGENT SUCTION PORT FILTER CLEANING | ☑ ELECTRODE REPLACEMENT<br>☑ ELECTRODE TUBE REPLACEMENT |

[Fig. 4a]

| MAINTENANCE ITEM | ORDER OF DIVIDED PROCEDURE ELEMENTS | CYCLE | AUTOMATIC MAINTENANCE | PORTION | REQUIRED TIME | CONDITION OF APPARATUS |
|---|---|---|---|---|---|---|
| REACTION PARTS WASHING | (A5) REACTION PARTS CLEANING<br>(A6) PERFORM CELL BLAND MEASUREMENT | 1 WEEK | ○<br>○ | REACTION DISK | 15 MIN<br>17 MIN | STANDBY |
| CELL COVER CLEANING | (A7) REMOVE CELL COVER<br>(A8) WIPE WITH GAUZE<br>(A11) MOUNT CELL COVER | 1 WEEK |  | REACTION DISK | 2 MIN<br>3 MIN<br>2 MIN | STANDBY |
| WASHING TANK CLEANING | (A15) WIPE WASHING TANK WITH COTTON APPLICATOR | 1 WEEK |  | COMMON TO UNIT | 5 MIN | STAND BY |
| WATER SUPPLY TANK CLEANING | (C3) TURN POWER OF APPARATUS OFF<br>(C8) REMOVE WATER SUPPLY TANK<br>(C10) PUT WATER IN WATER SUPPLY TANK<br>(C11) RETURN WATER SUPPLY TANK TO ORIGINAL POSITION | 1 WEEK |  | WATER SUPPLY AND DRAIN | 5 MIN<br>3 MIN<br>3 MIN<br>2 MIN | POWER OFF |
| REACTION CELL REPLACEMENT | (A7) REMOVE CELL COVER<br>(A9) REMOVE REACTION CELL<br>(A10) MOUNT REACTION CELL<br>(A11) MOUNT CELL COVER<br>(A5) REACTION PARTS WASHING<br>(A6) PERFORM CELL BLANK MEASUREMENT | 1 MONTH | ○<br>○ | REACTION DISK | 2 MIN<br>3 MIN<br>5 MIN<br>2 MIN<br>20 MIN<br>17 MIN | STANDBY |

[Fig. 4b]

| MAINTENANCE ITEM | ORDER OF DIVIDED PROCEDURE ELEMENTS | CYCLE | AUTOMATIC MAINTENANCE | PORTION | REQUIRED TIME | CONDITION OF APPARATUS |
|---|---|---|---|---|---|---|
| REACTION TANK CLEANING | (A12) START REACTION TANK CLEANING (FROM DISPLAY) | 1 MONTH | ○ | REACTION DISK | 1 MIN | STANDBY |
| | (A7) REMOVE CELL COVER | | | | 2 MIN | |
| | (A9) REMOVE REACTION CELL | | | | 3 MIN | |
| | (A13) WIPE REACTION TANK WITH GAUZE | | | | 5 MIN | |
| | (A10) MOUNT REACTION CELL | | | | 3 MIN | |
| | (A11) MOUNT CELL COVER | | | | 2 MIN | |
| | (A14) INSTRUCT WATER SUPPLY TO APPARATUS | | | | 1 MIN | |
| | (A6) PERFORM CELL BLANK MEASUREMENT | | | | 17 MIN | |
| BIFURCATED TUBE FILTER CLEANING | (C3) TURN POWER OF APPARATUS OFF | 1 MONTH | ○ | WATER SUPPLY AND DRAIN | 5 MIN | POWER OFF TO STANDBY |
| | (C4) REMOVE AND WASH BIFURCATED TUBE FILTER | | | | 3 MIN | |
| | (C5) RETURN BIFURCATED TUBE FILTER TO ORIGINAL POSITION | | | | 2 MIN | |
| | (C1) TURN POWER ON | | | | 5 MIN | |
| | (A18) PERFORM REACTION TANK WATER REPLACEMENT | | | | 10 MIN | |

[Fig. 4c]

| MAINTENANCE ITEM | ORDER OF DIVIDED PROCEDURE ELEMENTS | CYCLE | AUTOMATIC MAINTENANCE | PORTION | REQUIRED TIME | CONDITION OF APPARATUS |
|---|---|---|---|---|---|---|
| WASHING TANK CLEANING | (A15) WIPE WASHING TANK WITH COTTON APPLICATOR | 1 WEEK | | COMMON TO UNITS | 5 MIN | STAND BY |
| ISE REAGENT FLOW PATH WASHING | (D1) REPLACE REAGENT BOTTLE BY DETERGENT<br>(D2) START ISE REAGENT FLOW PATH WASHING (FROM DISPLAY)<br>(D3) REMOVE AND WASH SUCTION PORT FILTER<br>(D4) RETURN SUCTION PORT FILTER TO ORIGINAL POSITION<br>(D5) REPLACE DETERGENT BY WATER<br>(D6) WATER WASHING BY FUNCTION KEY<br>(D7) RETURN WATER TO REAGENT<br>(D8) PERFORM REAGENT PRIME<br>(D9) PERFORM ISE CHECK | 1 MONTH | ○<br><br><br><br>○<br>○ | ISE UNIT | 5 IN<br>1 MIN<br><br>3 MIN<br>2 MIN<br>3 MIN<br>3 MIN<br>2 MIN<br>5 MIN<br>5 MIN | STANDBY |
| REAGENT SUCTION PORT FILTER CLEANING | (D3) REMOVE AND WASH SUCTION PORT FILTER<br>(D4) RETURN SUCTION PORT FILTER TO ORIGINAL POSITION | 1 MONTH | | ISE UNIT | 3 MIN<br>2 MIN | STANDBY |
| ELECTRODE REPLACEMENT | (D10) OPEN TOP COVER AND ELECTRODE COVER<br>(D11) REMOVE CORD AND LEVER AND REPLACE ELECTRODE<br>(D12) MOUNT ELECTRODE AND RETURN CORD AND LEVER TO ORIGINAL POSITION<br>(D13) CLOSE TOP COVER AND ELECTRODE COVER<br>(D8) PERFORM REAGENT PRIME<br>(D9) PERFORM ISE CHECK | 2 MONTHS | <br><br><br>○<br>○ | ISE UNIT | 1 MIN<br>2 MIN<br><br>3 MIN<br><br>2 MIN<br>5 MIN<br>5MIN | STANDBY |
| ELECTRODE TUBE REPLACEMENT | (D10) OPEN TOP COVER AND ELECTRODE COVER<br>(D14) PULL OUT AND REMOVE BOTH ENDS OF ELECTRODE TUBE<br>(D15) INSERT NEW TUBE<br>(D13) CLOSE TOP COVER AND ELECTRODE COVER<br>(D9) PERFORM ISE CHECK | 2 MONTHS | <br><br><br><br>○ | ISE UNIT | 1 MIN<br>3 MIN<br><br>3 MIN<br>3 MIN<br>5 MIN | STANDBY |

[Fig. 5]

SORTING RULE
(1) DO NOT CHANGE ORDER OF DIVIDED PROCEDURE ELEMENTS AND DO NOT DELETE PROCEDURE ELEMENTS NOT DUPLICATED
(2) PERFORM PROCEDURE IN POWER OFF FIRST AS CONDITION OF APPARATUS FOR PERFORMING MAINTENANCE
(3) WHEN THERE IS PROCEDURE TO BE PERFORMED IN STANDBY STATE AFTER MAINTENANCE IN POWER OFF STATE, INSERT PROCEDURE OF POWER ON
(4) INTEGRATE SAME PROCEDURE ELEMENTS INTO A WHOLE
(5) GET SAME PORTIONS OR UNITS TOGETHER
(6) IF (2) TO (5) ARE UNDER SAME CONDITIONS, PERFORM MAINTENANCE HAVING SHORTER MAINTENANCE INTERVALS FIRST
(7) IF THERE IS PRESCRIPTION IN ORDER OF PERFORMANCE AMONG A PLURALITY OF MAINTENANCE ITEMS AS DESCRIBED BELOW, FOLLOW PRESCRIPTION (EXAMPLES ARE LISTED BY ASTERISKS)
  * IF CELL BLANK MEASUREMENT AND CELL REPLACEMENT ARE SELECTED, PERFORM CELL BLANK MEASUREMENT LATER
  * IF CELL BLANK MEASUREMENT AND POWER SOURCE LAMP REPLACEMENT ARE SELECTED, PERFORM CELL BLANK MEASUREMENT LATER
  * IF REACTION SYSTEM WASHING AND CELL BLANK MEASUREMENT ARE SELECTED, PERFORM CELL BLANK MEASUREMENT LATER
  * IF REACTION SYSTEM WASHING AND CELL REPLACEMENT ARE SELECTED, PERFORM REACTION SYSTEM WASHING LATER

[Fig. 6a]
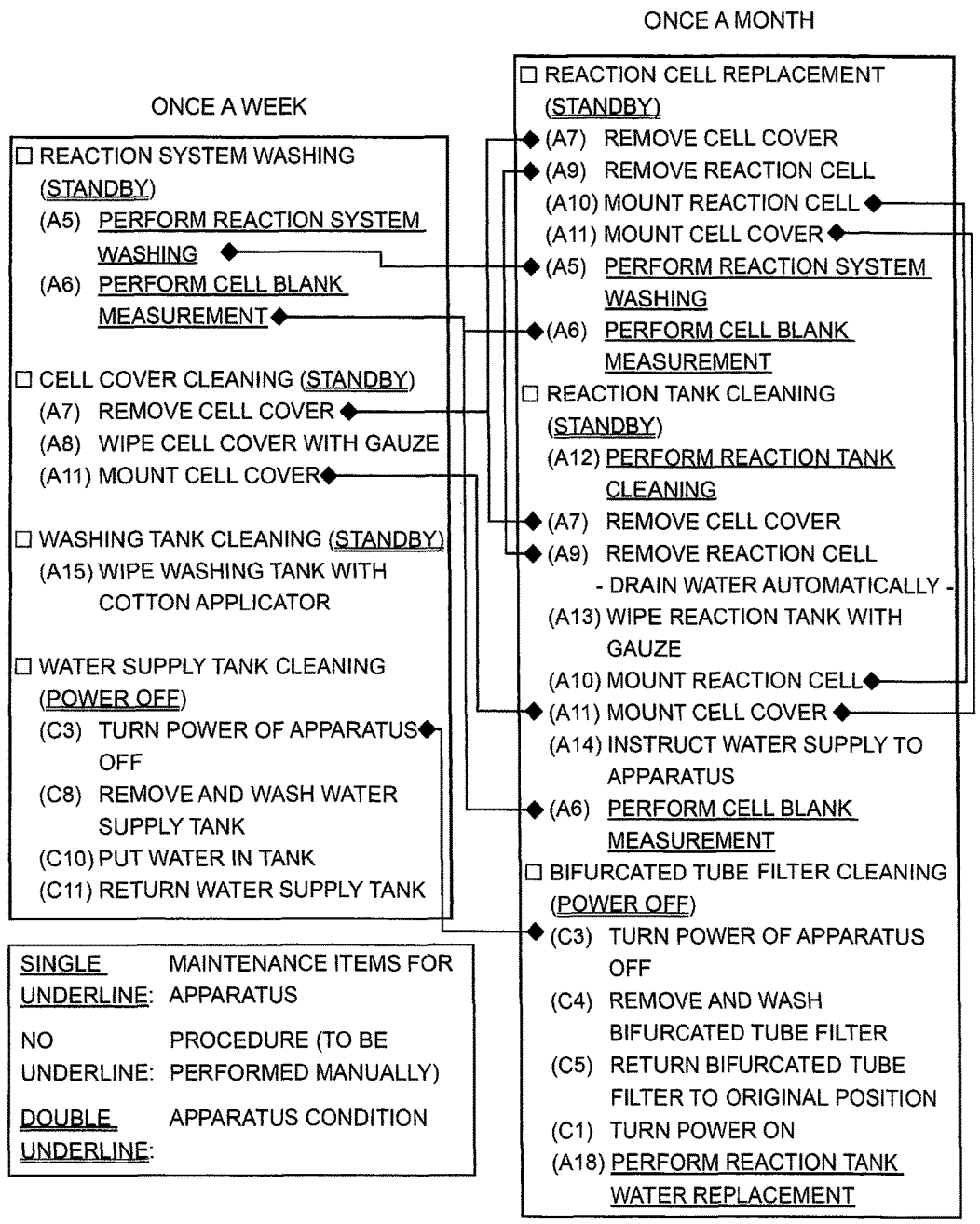

[Fig. 6b]
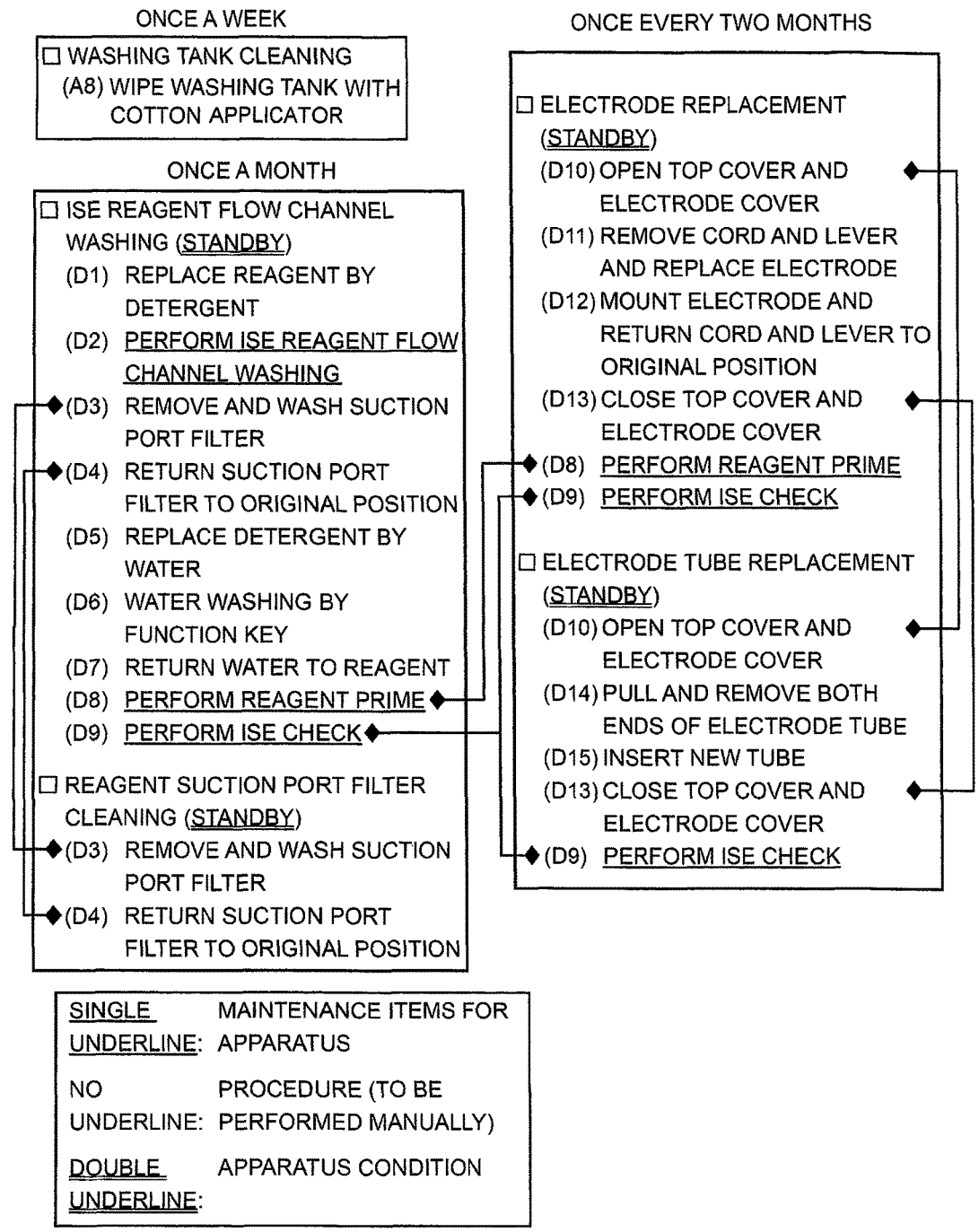

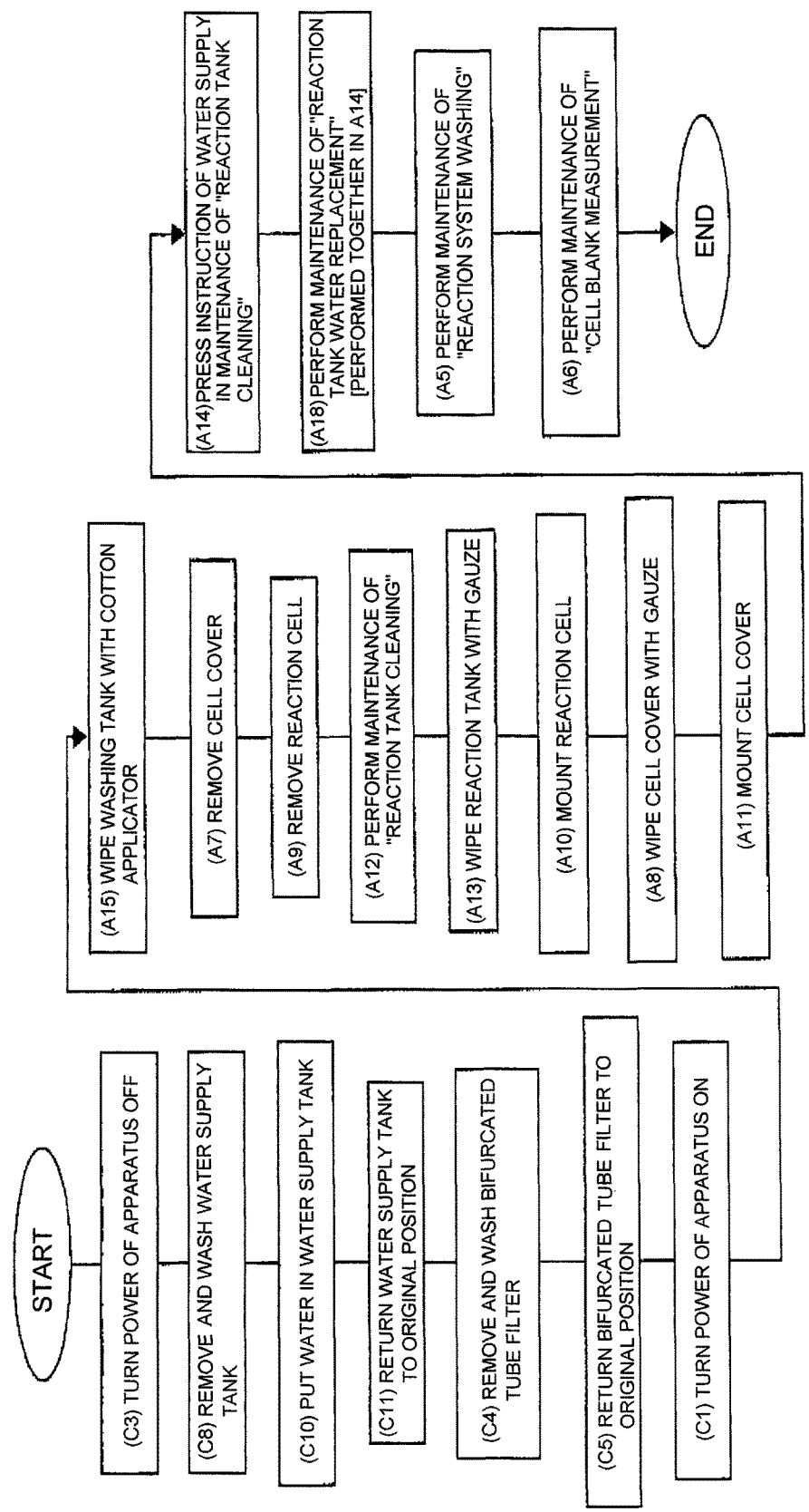
[Fig. 7a]

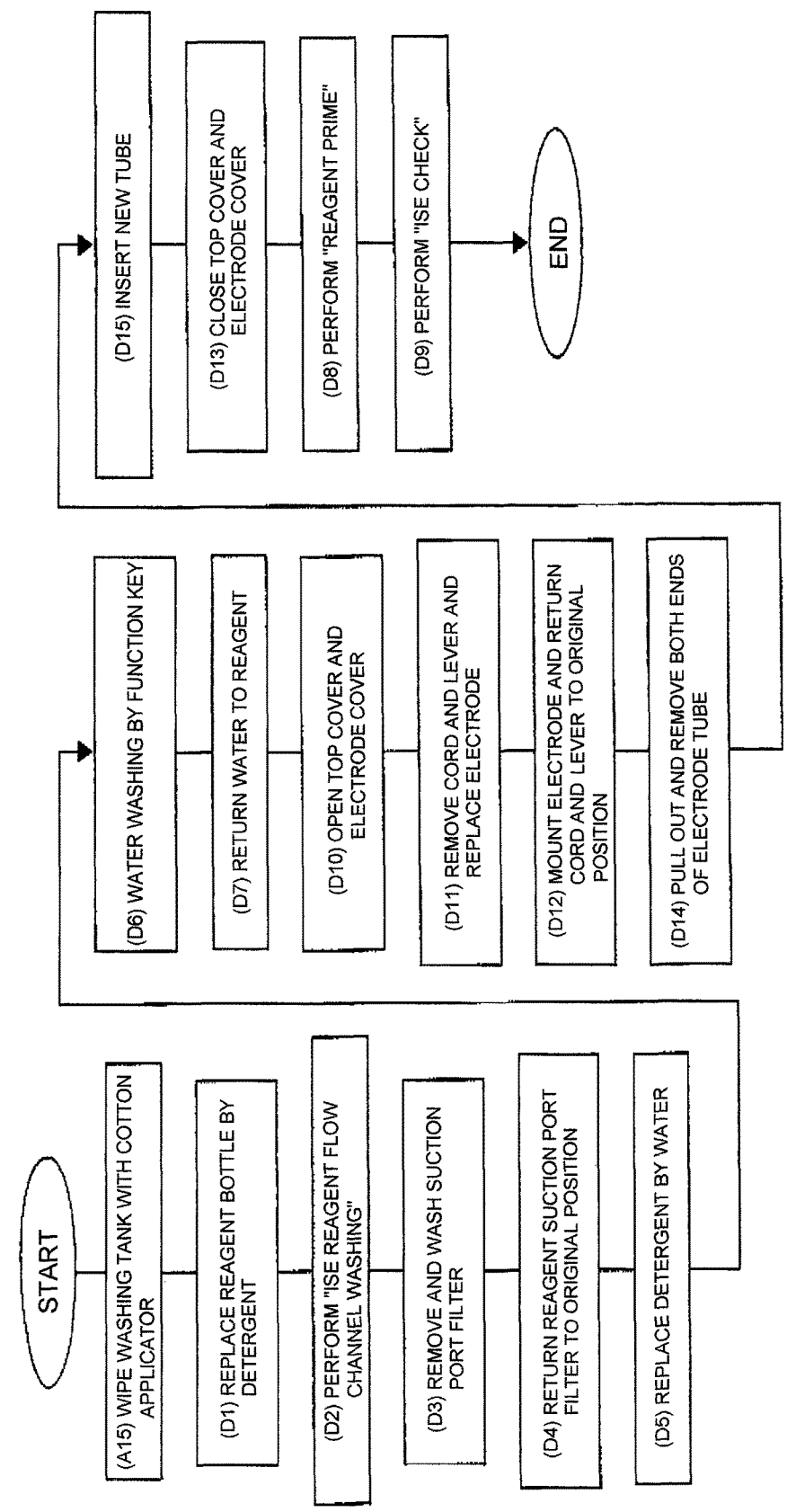
[Fig. 7b]

[Fig. 8]
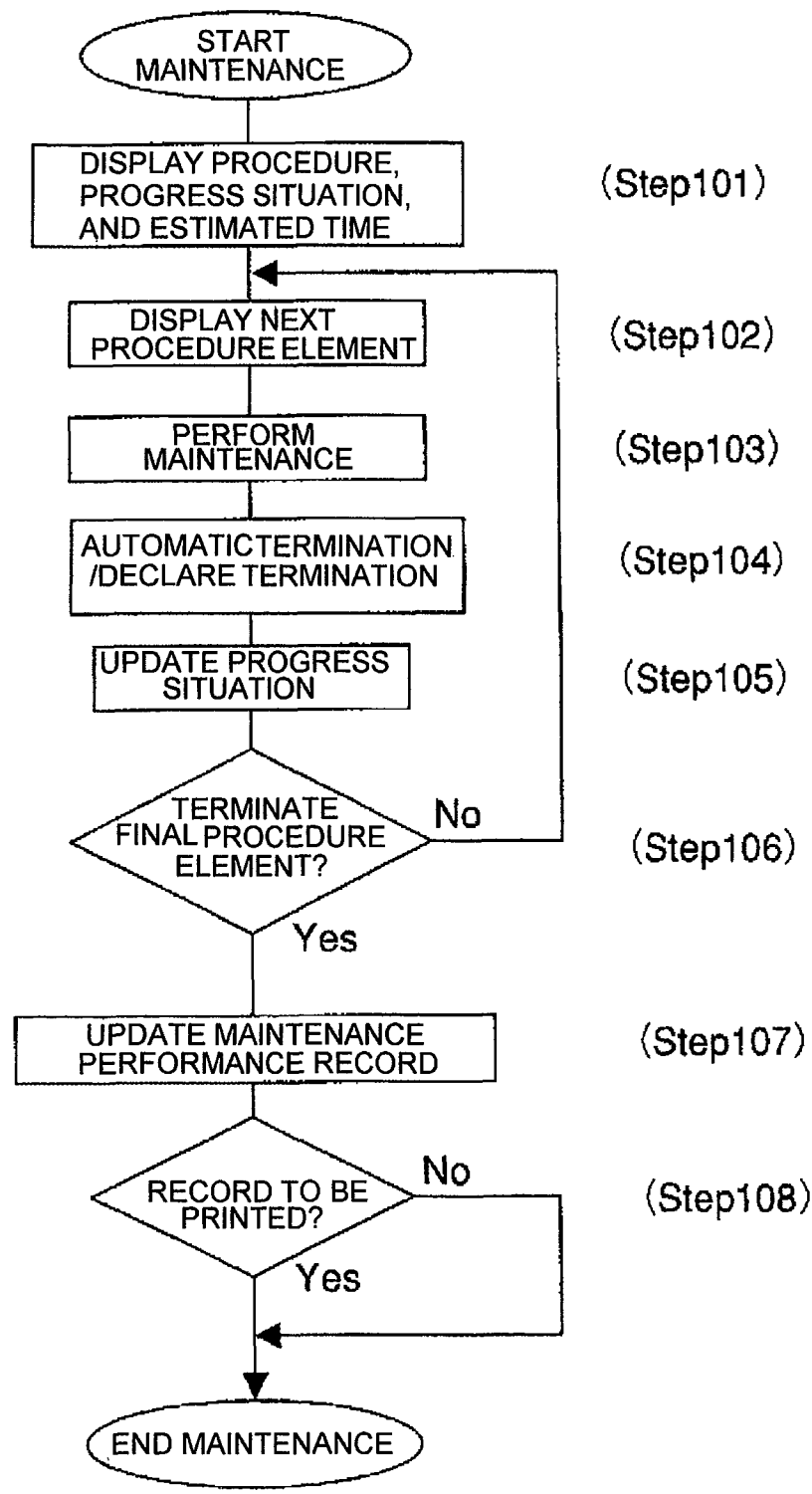

[Fig. 9]
(a)
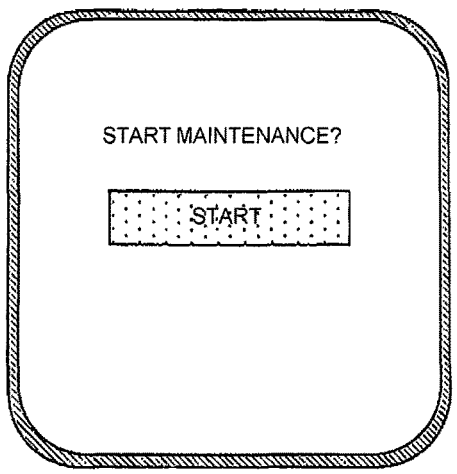
(b)
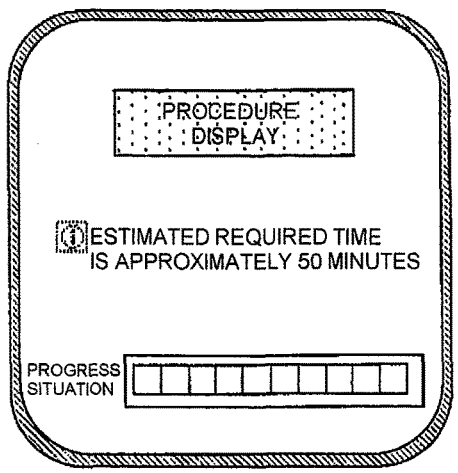
(c)
(d)
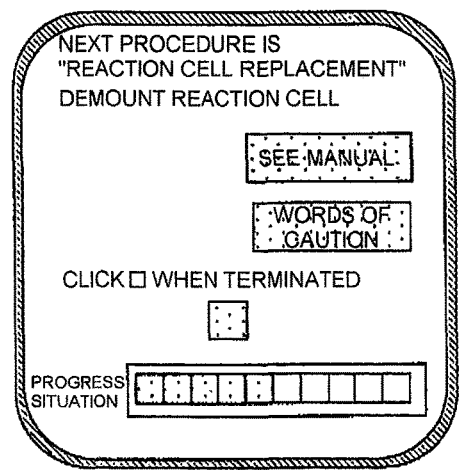
(e)
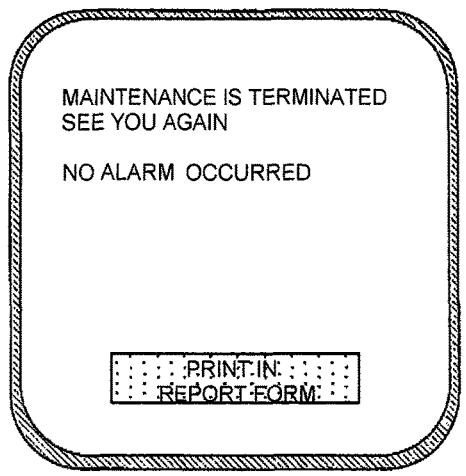

ANALYZING DEVICE

TECHNICAL FIELD

The present invention relates to an analyzing device requiring a plurality of items of maintenance different in frequency of performance and, more specifically, to an analyzing device provided with a function of recommending optimal maintenance depending on timing of performance of the maintenance.

BACKGROUND ART

Regular maintenance of an apparatus is a work required for maintaining performances of the apparatus. Facilities provided with an analyzing device configured to perform analyses of solid substances, liquids, and gases installed therein achieve maintenance of an analyzing performance and preventive maintenance of the apparatus by performing the maintenance at intervals recommended by manufacturers of the apparatuses.

Although the present invention is applicable to various types of analyzing devices, an analyzing device for clinical examinations will be exemplified for description given below. For apparatuses corresponding to specified maintenance apparatuses among medical apparatuses, it is absolutely necessary to perform maintenance of the apparatuses at intervals recommended by manufacturers of the apparatuses and keep records thereof.

Recently, hospitals and laboratories are now suffering financially due to lowering of NHI points. In contrast, medical facilities are required to provide a round-the-clock schedules and service improvement for patients. As support on the side of the laboratories, support on holidays and night-time shifts are in place. However, if an apparatus is installed, the number of personnel is reduced. Since a full-time personnel system cannot be prepared for each of the apparatuses, a plurality of apparatuses are operated by a single stuff and a personnel being short on experience and inexperienced may be tasked with performing the maintenance in many cases. A small number of service engineers are required to manage a large area and specific engineers for the product cannot be staffed in present conditions.

A procedure of maintenance is described in a paper-based manual or in HELP built in an operating unit of the apparatus. An operator performs maintenance according to the procedure described in the manual or the like in the procedures on the item-to-item basis.

The types of the maintenance may mainly be categorized into washing and part replacement. Also, the maintenance includes maintenance to be performed automatically by the apparatus, and items to be performed manually by the operator. Washing includes items which can be performed automatically, and items to be performed manually. The apparatus is capable of storing a record of items to be performed automatically in a storage unit of the apparatus and performing deadline management. There are apparatuses having a function to notify the fact that the performance deadline is close or passed by color or the like and alerting users. Also, some of the apparatuses are configured to prepare a maintenance table including maintenance items to be performed manually and keep a record unlike the automatic items. In such a case, it is necessary to perform the maintenance while checking a condition of measurement of the apparatus so as not to affect measurement of a sample. Also, when the mechanism of the apparatus becomes complicated, the number of maintenance items to be performed is increased and, specifically, for operators being short of experience on the apparatus, it will be hard to perform accurately.

In such circumstances, in Patent Literature 1, there is proposed that a record of operation of the medical apparatus up to the present time and abnormal information relating to abnormalities occurred in the past are kept and managed, and an operating state of the medical apparatus according to the elapsed time of operation of the medical apparatus and the conditions of occurrence of abnormalities is displayed. According to this technology, a short-term or long-term operating condition maybe displayed. The more the apparatus is complicated, the more the operating conditions are difficult to be figured out at a level of a person in charge, and hence showing by using a chart helps to figure out easily. However, efficiency of the individual procedures is not taken into consideration.

CITATION LIST

Patent Literature

PTL1: JP-A-2007-68721

SUMMARY OF INVENTION

Technical Problem

The frequencies of performance of the maintenance are different such as once a week or once a month since operating time intervals, degradation or conditions of abrasion of parts to be replaced, and the degree of adhesion of dirt on the parts due to the difference in characteristics of samples and reagents are different. Since the deadline recommended by the manufacturer depends on a standard time (operating time: 5 hours, power distribution: 8 hours, for example), it is necessary to adapt a maintenance plan in accordance with the operations thereof in the respective facility. The procedures of performance of the maintenance include those limited by the state of the apparatus.

The maintenance is performed while checking up the maintenance items to find efficient procedure every time because the combination of the selected items is not necessarily the same every time. Although performance with efficient procedure becomes possible with experience, if the inexperienced operator performs items one by one according to a manual, there is a case where the same procedures may arise by a plurality of times, and duplication of effort may result.

Some facilities fix up a maintenance program in advance. However, the procedure is not necessarily progressed as planned in case of a sudden trouble or depending on the conditions of measurement of the apparatus. In such a case, the maintenance items to be performed need to be changed and the procedure needs to be checked up again. These all become a burden on the operator. When the operator has a duty of a maintenance work from the evening in spite of being tired from a sample measurement work during the daytime, the operator gets more and more tired. On an assumption that there is a request of measurement along the way, maintenance of a plurality of apparatuses cannot be performed at once.

In addition, among the maintenance items, there are many items being complicated in procedure. If a confirming operation is neglected after the replacement of a part, there may be a case where an alarm is activated when starting the apparatus for the next time, and hence the task must be done over again. The task is difficult while looking a thick manual set aside.

The procedure of the maintenance is written in the manual. Since the manual is not written on the assumption that a plurality of the maintenance items are performed at once, the procedure is described from one maintenance item to another. However, if the manual is written on the assumption that a plurality of the maintenance items are performed at once, the number of pages of the manual is increased because a plurality of combinations are considered, and readability is impaired. The procedure that the operator wants to know is the procedure for performing a plurality of the maintenance items selected actually efficiently. However, in a case where the maintenance items to be selected are changed almost every time, it cannot be achieved.

If the operator has experience and knowledge about the apparatus, when performing a plurality of the maintenance items, the operator can perform with an efficient procedure. In order to do so, the operator reads the manual in advance and considers the procedure before performing, and hence time and effort are demanded for advance preparation.

In addition, among the maintenance items, there are items that cannot be stopped along the way when started once. When the maintenance that takes time is started, the operator may not be capable of doing other things until it is normally terminated. Since an estimated time required for the maintenance is unknown, the operator can hardly set a schedule.

Maintenance management of the apparatus is performed by the operator or an administrator on the basis of the control table or the like. Since the maintenance performed by the apparatus may be transferred after the performance as well because there is a performance record. The maintenance to be performed manually is performed only on the basis of the maintenance table. There is a case where the operator who had performed forgets about it. Although reliable maintenance is required, the manual maintenance items which cannot be preserved as the record account 50 to 70% of the entire part, and the method of management is complicated and the burden on the operator is great.

It is an object of the present invention to provide an analyzing device having a plurality of maintenance items that is capable of performing maintenance efficiently with no waist.

Solution to Problem

A configuration of the present invention in order to achieve the above-described problem is as follows.

An analyzing device including: storage means configured to store a plurality of maintenance items and intervals for performing the maintenance for each of the maintenance items; maintenance performance instructing means configured to instruct performance of maintenance; extracting means configured to extract maintenance items to be performed at a time point when the instruction is issued by checking up the intervals of performance of the maintenance stored in the storage means upon reception of an instruction to perform the maintenance from the maintenance instructing means; sorting means configured to sort the maintenance items extracted by the extracting means in the order of performance of the maintenance on the basis of a predetermined rule; and display means configured to display the maintenance items in the order sorted by the sorting means.

Another configuration of the present invention is an analyzing device including means for storing a plurality of procedure elements from one maintenance item to another of the analyzing device and storing a rule for sorting the procedure elements, selecting means configured to select a maintenance item by a unit of the maintenance item; and a control unit configured to cause display means to display the procedure elements of the maintenance item selected by the selecting means by arranging in conformity to the rule.

The maintenance items mean operations/actions required for causing the analyzing device to act normally. In a case of an automatic analyzing device for clinical inspection, there are the one performed by an operator such as operation to clean a dispensing nozzle for dispensing a predetermined amount of sample or reagent and the one performed automatically by a machine such as washing of a reaction container and a purging action for removing air bubbles in a dispensing channel or the like.

The present invention causes the maintenance items to be performed to be displayed in the order of performance, which is not limited to those performed by the operator, and in a case where the maintenance items to be performed by the operator and the maintenance items to be performed by the machine both exit for example, an analyzing device including means for displaying the both together in the order to be performed.

Advantageous Effects of Invention

According to the present invention, when performing maintenance, it is no longer necessary to consider an efficient maintenance procedure by confirming the procedure manually in advance. In other words, a labor and an operating time required for the maintenance operation by itself may be reduced for allowing main assignment of the analyzing operation to be concentrated. Also, the analyzing device including a function of complying with regular performance of maintenance and reliably performing preventive maintenance may be provided. According to the present invention, stable operation of the apparatus may be supported by adding this function.

BRIEF DESCRIPTION OF THE DRAWINGS

FIG. 1 is a general configuration drawing.
FIG. 2 is a procedure integration flow.
FIG. 3a illustrates an example of a screen for selecting maintenance items.
FIG. 3b illustrates the example of the screen for selecting the maintenance items.
FIG. 4a is procedure element information on the maintenance items.
FIG. 4b is procedure element information on the maintenance items.
FIG. 4c is procedure element information on the maintenance items.
FIG. 5 is a sorting rule list.
FIG. 6a is a detailed example for selecting the maintenance items.
FIG. 6b is a detailed example for selecting the maintenance items.
FIG. 7a is an example after the element procedure sorting.
FIG. 7b is an example after the element procedure sorting.
FIG. 8 is a maintenance performance flow.
FIG. 9 is an example of performance on a mobile terminal.

DESCRIPTION OF EMBODIMENT

Referring now to the drawings, an example of the present invention will be described.

FIG. 1 illustrates an appearance of an analyzing device. The analyzing device illustrated in FIG. 1 mainly includes a sample disk 1, a reagent disk 2, a reaction disk 3, a reaction tank 4, a sampling mechanism 5, a reagent pipetting mechanism 6, an agitating mechanism 7, a photometry mechanism 8, a washing mechanism 9, a display unit 10, an input unit 11, a storage unit 12, and a control unit 13.

In FIG. 1, a plurality of sample containers 16 in which obtained samples are placed are fixedly arranged on a circumference of a circular disk 17 on the sample disk 1. The circular disk 17 is capable of rotating in the circumferential direction and stopping at a predetermined position by a drive mechanism composed of a motor and a revolving shaft or the like, not illustrated.

In FIG. 1, a plurality of reagent bottles 18 in which reagent to be mixed with the samples to react is put are fixedly arranged on a circumference of a circular disk 19 on the reagent disk 2, and the periphery of the reagent bottles 18 is a temperature-controlled cool box 20.

The circular disk 19 rotates in the circumferential direction so as to be capable of positioning by the drive mechanism composed of the motor and the revolving shaft, not illustrated.

In FIG. 1, a plurality of reaction container holders 22 in which reaction containers 21 in which the sample and the reagent are put are held are mounted on the reaction disk 3, and the reaction disk 3 repeats circumferential rotation and stop at certain cycles and transfers the reaction containers 21 intermittently by a drive mechanism 23.

In FIG. 1, the reaction tank 4 is a constant temperature reservoir installed along a locus of movement of the reaction containers 21, and configured to control reaction solution in the reaction containers 21 at a constant temperature, for example, by temperature-controlled constant temperature water in order to accelerate a chemical reaction between samples and reagent. The reaction containers 21 move in the reaction tank 4.

In FIG. 1, the sampling mechanism 5 includes a probe 24, an arm 26 mounted on a rotatably supporting shaft 25, and a drive mechanism which allows a reciprocal motion between the sample disk 1 and the reaction disk 3 about the rotatably supporting shaft 25 as a center of rotation.

The sampling mechanism 5 supplies samples in the sample containers 16 transferred to fixed positions along with a rotation of the sample disk 1 to the reaction containers 21 according to a predetermined sequence.

In the same manner as the sampling mechanism 5 described above, the reagent pipetting mechanism 6 includes a probe 27, an arm 29 mounted on a rotatably supporting shaft 28 and a driving mechanism which allows a reciprocal motion between the reagent disk 2 and the reaction disk 3 about the rotatably supporting shaft 28 as a center of rotation.

The reagent pipetting mechanism 6 supplies reagent in the reagent bottles 18 transferred to fixed positions along with a rotation of the reagent disk 2 into the reaction containers 21 according to a predetermined sequence.

In each of the sample containers 16 and the reagent bottles 18, the samples and the reagents of different types are placed, and the required amount is supplied to the reaction containers 21. The reaction solution in the reaction containers 21 is agitated by acoustic waves emitted from a piezoelectric element 31 of the agitating mechanism 7 every time when the reagent is placed. Although the agitating mechanism on the basis of an ultrasonic wave is illustrated, an agitating mechanism on the basis of an agitating rod is also possible.

The reaction containers 21 are washed by a washing nozzle of the washing mechanism 9 after measurement by the photometer 8, and are used for the next measurement.

In FIG. 1, the display unit 10 performs various screen displays such as items of analysis, results of analysis, and the state of performance of the maintenance or the like. The display unit 10 includes a monitor connected to a personal computer, and a mobile terminal display unit 35 which is transmittable without wires as parts of the display unit. The mobile terminal display unit 35 has not only a role of the display unit, but also a function capable of exchanging information with respect to the storage unit within the device via the control unit and giving an instruction of operation to the control unit. It is also possible to store the information in a storage unit of a mobile terminal.

The input unit 11 input the various items of information such as the items of analysis, and the reagent. The storage unit 12 stores various items of information such as a sequence (program) determined in advance for controlling various mechanisms and the items of analysis. In addition to the illustration in FIG. 1, a syringe, a pump, and the like are included as components, and all the components including these components are controlled by the control unit 13 according to the sequence stored in the storage unit 12.

The storage unit 12 may include two types; that is, a storage device in the interior of the device, and a storage device in a personal computer as an operating unit. In such a case, the storage unit 12 in the analyzing device is always connected to the storage unit 12 of the operating unit via a communication cable or without wires for passing information.

This example is an example in which the storage device in the personal computer in the operating unit is used as the storage unit 12. The display unit 10 illustrated in FIG. 1 is capable of connecting a CRT display or a liquid crystal monitor or the like.

The storage unit 12 includes information on maintenance item procedure element 40 to be performed by the device, and a sorting rule list 41 as judgment logic for converting the same into a series of maintenance procedures stored therein.

The storage unit 12, a logical judgment unit, and a maintenance performance instruction unit may be arranged together or separately in the analyzing device respectively, or may be arranged in an external device different from the analyzing device connected to the analyzing device via a wire or without wires.

Referring now to FIG. 2, the information on maintenance item procedure element 40 stored in the storage unit will be described. In the device, regular maintenance is required for maintaining the performance thereof. A maintenance deadline is set with reference to the deadline instructed by manufacturer, and is managed and performed. As illustrated in an example of description in a manual of maintenance deadline management function in Reference 1, dates when the maintenance is successfully performed may be confirmed by the display unit 10 or the mobile terminal display unit 35, and a maintenance performance record 42 to which dates when the maintenance corresponding to the respective maintenance items and information on presence or absence of alarm generation are added are stored in the storage unit 12. In addition, deadlines of performance at a notification level and a caution level are set from the input unit 11, this setting is stored in the storage unit 12 as deadline management information 43, and the display unit 10 is configured to be capable of determining deadline management by color or the like as needed.

The performance flow of the present invention will be described with reference to FIG. 2. When performing the maintenance items by the apparatus, selection of the maintenance items is performed from the input unit 11 or the mobile terminal display unit 35 (Step 1). Subsequently, whether or not the selected item or items is or are single or plural is determined (Step 2). In the case of the single item, since a procedure to combine the procedures is not necessary, the procedure goes to a procedure display (Step 8). If a plurality of the items are selected, the selected maintenance items are divided into procedure elements (Step 3). Actually, as regards Step 3, the procedure elements divided in advance are stored in the storage unit 12 or the mobile terminal display unit 35 of the device. Subsequently, whether or not there are items different in conditions to perform the maintenance, whether or not there are duplicated procedures in the divided procedure elements, and whether or not there is a preferential order are checked up with the sorting rule list 41 (Step 4 and Step 5). Depending on the result, the sorting of the procedure elements is performed (Step 6). A time required for the sorted procedure elements is multiplied (Step 7). Finally, a series of the procedure elements calculated in Step 6 and an estimated required time are displayed (Step 8).

The selection of the maintenance items in Step 1 will be described with reference to the examples in FIG. 3a and FIG. 3b. Lists of the items of the regular maintenance are displayed on the frequency-by-frequency basis, and the maintenance items are displayed from one frequency to another. There are means that allow selection for each item (check box or the like), and a plurality of items may be selected by selecting the same. The frequency may be changed by arrow keys or the like. FIG. 3a is an example of the maintenance items mainly for a colorimetric analyzer, and FIG. 3b is the same mainly for an electrolyte analyzer (ISE) unit. Hereinafter, description will be given on the basis of the case where the items illustrated in FIG. 3a and FIG. 3b are selected.

Division of the maintenance into the procedure elements in Step 3 is listed in advance and is stored in the storage unit 12. The listed information of maintenance items will be described with reference to examples in FIG. 4a, FIG. 4b, and FIG. 4c. FIG. 4a and FIG. 4b illustrate information on procedure elements of the maintenance items selected in FIG. 3a, and FIG. 4c illustrates information on procedure elements of the maintenance items selected in FIG. 3b.

The information on maintenance item procedure element 40 including maintenance items and the procedure elements divided for performing the maintenance are saved in the storage unit 12 in the order of performance, and the information on maintenance item procedure element 40 includes portions, whether or not the maintenance is performed automatically, a required time, and conditions of the apparatus as other items of information. Such information is saved in one to one correspondence with the maintenance performance record 42 such as the date of performance (the date of success of the previous time) and the deadline management information 43 which sets performance intervals set in advance, the display is changed depending on the level of the performance deadline, or at the time of performance, the date of performance is updated (Step 107 in FIG. 8).

The sorting in Step 4 and Step 5 are stored in the storage unit 12 as the sorting rule list 41 in advance. The sorting rule list 41 will be described with reference to an example in FIG. 5. Depending on the sorting rule list 41, the order of the procedures is determined. Basically, the order of the element procedures is not changed, and the procedure elements which are not duplicated are not deleted (Rule (1)). First of all, sorting out is performed depending on the condition of the apparatus on which the maintenance is started. The procedure elements to be performed in a state of power OFF are performed first (Rule (2)). Subsequently, if there is maintenance to be performed in a stand-by state, the procedures to be performed with power ON are added (Rule (3)).

If the same procedure elements are included, they are put together into a whole (Rule (4)). Items are put together by portion or unit (Rule (5)). If Rules (2) to (5) are in the same conditions, priority is placed on the items having shorter maintenance intervals (Rule (6)). If the items are not narrowed down, however, a rule, such as following the order in the list, is established in advance. In addition, if there is a restriction in order of performance between the individual maintenance items, a rule therefor is also established (Rule (7)). For example, the rule is such that if a cell blank measurement and a cell replacement are selected, the cell blank measurement is performed later. The reason why the rules described thus far are needed will be described in detail in maintenance integration from FIG. 6a to FIG. 7a, and maintenance integration from FIG. 6b to FIG. 7b.

The procedure of sorting will be descried with detailed examples. FIG. 6a is an example of selection from the maintenance items in FIG. 3a, FIG. 4a, and FIG. 4b. Reaction system washing, cell cover cleaning, washing tank cleaning, and water supply tank cleaning are selected from a once-a-week list. Reaction cell replacement, cleaning of a reaction tank, and cleaning of a bifurcated tube filter are selected from once-a-month list. The element procedures of the respective items are assigned with signs (A5 to A15, A18, C1, and C3 to C5, C8, C10, and C11). FIG. 6b is an example of selection from the maintenance items in FIG. 3b and FIG. 4c. The washing tank cleaning is selected from once-a-week list. ISE reagent flow path washing, reagent suction port filter cleaning from the once-a-month list, and electrode replacement and electrode cube replacement are selected from an every-two-month list. The element procedures of the respective items are assigned with signs (A8, and D1 to D15).

A method of obtaining a series of procedures illustrated in FIG. 7a by sorting the maintenance items in FIG. 6a according to a sorting rule list illustrated in FIG. 5 will be described. The condition of the apparatus is such that the water supply tank cleaning and the bifurcated tube filter cleaning are to be performed in a state of power OFF, and hence these two items are performed first. This complies with Rule (2) in FIG. 5. Since the maintenance intervals are shorter in the case of the water supply tank cleaning, it is performed before the bifurcated tube filter cleaning. This complies with Rule (6) in FIG. 5. Since the conditions of the apparatus are confirmed after the maintenance in many cases, performing the maintenance with the power OFF first is efficient. One of the reasons is a background that time is required for starting up the power. Since the conditions of the apparatus are changed before the cleaning of the washing tank in (A15), a procedure of turning the power of the apparatus ON in (C) is inserted. This complies with Rule (3) in FIG. 5. After turning the power ON, the washing tank cleaning is performed first. It is because a reaction cell and a cell cover and the reaction tank are included in the same unit, and the washing tank cleaning has shorter maintenance intervals than the reaction cleaning (complies with Rules (5) and (6)). Rule (5) of performing the maintenance intensively by the same portion or unit has a merit that the movement of the operator from site to site may be reduced. The reason why the maintenance having shorter intervals is performed first is that a substantial need for strict compliance with the maintenance intervals exists. Therefore, since there may arise a case where the maintenance cannot be continued due to some troubles occurring in the apparatus, or a case where necessity of measurement of a general specimen material suddenly arises, the order of priority is preferably raised. Subsequently, the reaction tank water cleaning is performed. This maintenance is combined maintenance including a cleaning work and water replacement, and if a water supply instruction of (A14) is performed at the end of the reaction tank cleaning, the device performs the same process as (A18), and hence the necessity of performance of the reaction tank water replacement by itself is no longer necessary.

There are duplicated maintenance items (A5, A6, A7, A9, A10, and A11). The sorting is performed according to the rules and the procedure elements are combined into a whole. This complies with Rule (4) in FIG. 5. Performing mounting/demounting of the cell cover (A11/A7) and mounting and demounting of the reaction cell (A10/A9) several times makes no sense. If the operator is experienced to some extent, he or she may consider performing the operations once because it will be demounted at the time of the next maintenance. However, inexperienced users may not be capable of determining from the appellation of the maintenance in many cases. Display in the procedure integrated from the beginning is effective. When the rule cannot be complied with when performing a plurality of items, a series of procedure element orders having high priority are preferably input in advance. If the maintenance relating to the cell is performed, cell blank measurement is required as a confirming operation at the end. The operations such as cleaning or replacement are performed as a whole, and the cell blank measurement is performed for confirmation at the end (A6) (sorting in conformity to Rule (7)). When the order of performance has a meaning such that the confirming operation is performed later as described above, the order is preferably sorted in conformity to Rule (7) so as not to get wrong order. In the maintenance, there is a case where the maintenance is suspended and redone since the confirming operation to be performed at the end cannot be imagined from appellations of maintenance items. However, if it is found after the routine inspection has started, not only a waste of time as a matter of course, but also a delay of reporting the inspection to a patient may result. This is an important problem. In order to avoid neglect of confirmation, an inspection engineer is required to read a handling manual so as not to be leaked and faces with a dilemma such that the complexity cannot be resolved. However, by sorting the procedure elements efficiency in this manner, the complexity may be resolved.

In Step 6 in FIG. 6, sorting of the procedure elements is performed, and displayed on the display unit 10. The procedure elements after the sorting has performed according to the sorting rule list illustrated in FIG. 5 will be described in FIG. 7a. The procedure element (C3) "TURN OFF POWER OF APPARATUS" to the procedure element (A6) "PERFORM MAINTENANCE OF "CELL BLANK MEASUREMENT"" are displayed on the screen. A graphic indicating a progress situation and an estimated time are displayed in addition to the procedure. There is no duplicated procedure element, and the power ON/OFF operation is not needed more than once.

First of all, the reason why (C3) "TURN OFF APPARATUS" is sorted so as to come first is because the maintenance items "WATER SUPPLY TANK CLEANING" and "BIFURCATED TUBE FILTER CLEANING" are performed prior to other maintenance items in conformity to Rule (2). Then, in conformity to Rule (6), "WATER SUPPLY TANK CLEANING" having shorter maintenance cycle is performed first, the items are arranged in the order of (C3), (C8), (C10), and (C11). The reason why the order of the procedure element of "WATER SUPPLY TANK CLEANING" is not changed is because Rule (1) is complied with.

Subsequently, since "WATER SUPPLY TANK CLEANING" is terminated by (C11), "BIFURCATED TUBE FILTER CLEANING" continues subsequently. In conformity to Rule (4), (C3) "TURN OFF POWER OF APPARATUS" of "BIFURCATED TUBE FILTER CLEANING" is put together with (C3) of "WATER SUPPLY TANK CLEANING" into a whole. Therefore, in conformity to Rule (1), (C4), (C5), and (C1) are arranged in sequence without following (C11). Although (A18) is an automatic maintenance, and needs not to be displayed, it may be displayed by being integrated as needed.

Subsequently, the maintenance items "REACTION SYSTEM WASHING", "CELL COVER WASHING", "WASHING TANK CLEANING", "REACTION CELL REPLACEMENT", AND "REACTION TANK CLEANING" to be performed with the conditions of the apparatus being stand-by state continue. By considering Rules (4) to (7), the maintenance items are sorted to (A15), (A12), (A7), (A9), (A13), (A10), (A8), (A11), (A14), (A5), and (A6). If the preferential order is not determined even though Rules (4) to (7) are considered, the procedure elements may be sorted by regularizing the preferential order in advance or providing exception of the rule.

As a result of sorting in conformity to the sorting rule, 55 minutes could be shortened from an accumulated total of a required time illustrated in FIG. 4a and FIG. 4b (15 minutes for reaction system washing, 17 minutes×2 for cell blank, 4 minutes×2 for cell cover mounting/demounting, and 8 minutes for cell mounting/demounting).

Furthermore, as another example, a method of obtaining a series of procedures illustrated in FIG. 7b by sorting the maintenance items in FIG. 6b in conformity to a sorting rule list illustrated in FIG. 5 will be described.

There are duplicated maintenance items (D3, D4, D8, D9, D10, and D13). The sorting is performed according to the rules and the procedure elements are combined into a whole. This complies with Rule (4) in FIG. 5. The background of Rule (4) is as described above. The ISE check is necessary as a final confirming operation in the maintenance relating to the electrode. It is maintenance at the same positioning as the cell blank measurement described above. Such confirming maintenance is maintenance which can be performed by itself. In Step 6 in FIG. 6b, the sorting of the procedure elements is performed and is displayed on the display unit 10. The procedure elements after the sorting has performed according to the sorting rule list illustrated in FIG. 5 are shown in FIG. 7b. There is no duplicated procedure element, and the ISE check is not needed more than once.

As a result of sorting in conformity to the sorting rule, 19 minutes could be shortened from an accumulated total of a required time illustrated in FIG. 4c (5 minutes×2 for ISE check, 4 minutes for opening and closing the cover, and 5 minutes for mounting/demounting the filter).

Subsequently, a flow of performing maintenance will be described in FIG. 8. If a start button is touched in order to start the selected maintenance items, the procedure elements illustrated in FIG. 7, an indicator that indicates a progress situation, and an estimated required time are displayed (Step 101). If there are many procedure elements, it is not necessary to display a list.

The maintenance items are performed in the displayed order, and the completion of performance is declared for the performed procedure elements (Step 102, Step 103). The indicator indicating the progress situation is updated upon reception of declaration of the completion (Step 104), and then the next procedure element is displayed (Step 105).

Subsequently, Step 102 to Step 105 are repeated until the procedure elements are terminated. When the final procedure element is terminated (Step 106), the maintenance performance record 42 in the storage unit 12 is updated (Step 107). When needed, a record of the performed maintenance is printed out (Step 108), and the maintenance is terminated.

Although all the procedure elements may be displayed when a large display area is present, it is difficult to display the entire part by the display unit which is compact like a mobile terminal and supposed to be carried around. An example of a case of operating from the mobile terminal display unit 35 will be described with reference to FIG. 9(a) to FIG. 9(e). "START" maintenance is touched to start a series of integrated maintenance procedures (FIG. 9(a)). When a PROCEDURE DISPLAY button is touched, the estimated required time and the indicator indicating the progress situation are displayed (FIG. 9(b)). The PROCEDURE DISPLAY button is touched to display the maintenance procedure elements to be performed next (FIG. 9(c)). When reading of the manual is desired, a REFER TO MANUAL button is pressed for reference. When terminated, a square is touched to declare the completion of the maintenance. At a time point when the automatic maintenance items of the apparatus illustrated in FIG. 6 are normally terminated, subsequent procedure elements are displayed.

The indicator of the progress situation is updated to display the subsequent procedure elements. If there are words of caution in the procedure elements, a button to allow reference of the words of caution was installed (FIG. 9(d)). Although the inexperienced operators read the manual or the words of caution, the experienced operators do not refer thereto, and may finish the maintenance early.

When the last procedure elements are terminated, the termination is displayed, and items that are alarmed and not normally terminated, if any, are displayed (FIG. 9(e)). In a terminated stage, the maintenance performance record 42 in the storage unit 12 is updated. For facilities which print and record and file the performance record, a PRINT IN REPORT FORM button is provided to enable printing.

The information on maintenance item procedure element 40 and the sorting rule list 41 are stored in the storage unit 12 of the device and the sorting of the procedures is performed, so that the information on maintenance item procedure element 40, the sorting rule list 41, the maintenance performance record 42, and the deadline management information 43 may be saved not only in means for displaying on the mobile terminal display unit 35 but also in the mobile terminal, and a series of the sorted maintenance procedures integrated into a whole may be displayed and managed.

The present invention has been described thus far. In the example, the example in which Rules (1) to (7) are combined and sorted has been described. However, at least the effect of the present invention is achieved not necessarily by a configuration having all the rules, but by having one rule.

For example, a case where only Rule (2) is employed will be described. If the maintenance item in the power OFF state and the maintenance item in the stand-by state are selected, the procedure elements are sorted so that the maintenance in the power OFF state is performed first. Specifically, maintenance items to be performed in the power OFF state of the apparatus, and maintenance items to be performed in the power ON state of the apparatus are sorted so as to be performed respectively continuously. Therefore, improvement in efficiency of the maintenance is achieved without performing inefficient maintenance operation such that the maintenance in the power OFF state is performed, the maintenance in the stand-by state is performed, and then the maintenance is performed in the power OFF state again.

Also, for example, a case where only Rule (4) is employed will be described. If different maintenance items including common procedure elements are selected, the procedure elements of the selected maintenance item are sorted so that the same common procedure elements are integrated into a whole. Therefore, it is no longer necessary to perform the procedure elements redundantly, and hence improvement in efficiency of the maintenance is achieved. Specifically, when a first maintenance item including the procedure elements arranged in the order of the procedure elements A, B, and C, and a second maintenance item including the procedure elements arranged in the order of the procedure elements A, D, and C are selected, the control unit arranges the procedure elements in the order of A, B, D, and C or in the order of A, D, B, and C and displays the same on the display means. The order of B and D may be determined on the basis of maintenance intervals of Rule (6) or a rule determined in advance. For example, A, B, C, and D are (A7), (A8), (A9), and (A11), respectively.

Also, a case where only Rule (5) is employed will be described. In a case where a plurality of the maintenance items for the same portion or the unit are selected and the maintenance items are selected for the different portion or the unit, the sorting is performed so that the same portion or the unit are performed continuously. Therefore, since performance of the maintenance by returning to the portion or the unit for which the maintenance is performed once is eliminated, improvement of efficiency of the maintenance is achieved.

Also, as Rule (6), if items whose priority cannot be determined are included in the maintenance items, these items are sorted so that priority is placed on the maintenance items shorter in maintenance intervals. As described before, even in a case where any trouble of the apparatus occurs and hence the maintenance cannot be continued, or necessity of measurement of a general specimen material suddenly arises, keeping of the maintenance intervals is achieved thereby.

It is also possible to determine not only a single rule, but also a given rule in advance by combining the rules.

REFERENCE SIGNS LIST 1 sample disk
2 reagent disk
3 reaction disk
4 reaction tank
5 sampling mechanism
6 reagent pipetting mechanism
7 agitating mechanism
8 photometry mechanism
9 washing mechanism
10 display unit
11 input unit
12 storage unit
13 control unit 16 sample container
17, 19 circular disk
18 reagent bottle
20 cool box
21 reaction container
22 reaction container holder
23 drive mechanism
24, 27 probe
25, 28 rotatably supporting shaft
26, 29 arm
31 piezoelectric element
33 washing nozzle
35 mobile terminal display unit or maintenance performance instructing device (not necessarily be mobile)
40 information on maintenance item procedure element
41 sorting rule list
42 maintenance performance record
43 deadline management information

The invention claimed is:

1. An analyzing device for clinical examinations, comprising:
   a reaction system including a plurality of reaction cells;
   a storage device storing a plurality of maintenance items for the analyzing device, a plurality of predetermined time intervals for performing maintenance of each of the maintenance items, and a plurality of procedural elements that constitute each of the maintenance items, where two or more of the maintenance items include a same procedural element among the plural procedural elements;
   an extracting unit configured to, upon reception of an instruction to perform maintenance, extract the procedural elements of a set of two or more of the maintenance items to be performed on the basis of the time intervals stored in the storage device;
   a sorting unit configured to sort the extracted procedural elements of each of the maintenance items in the set into an order on the basis of predetermined rules;
   a display unit configured to display the sorted procedural elements of each of the maintenance items in the set in the sorted order; and
   a control unit programmed to control the reaction disk, the storage unit, the extracting unit and the sorting unit,
   wherein the control unit is further programmed to control the sorting unit to sort the extracted procedural elements based on the rules, which include:
   when the same procedural elements are included in the extracted procedural elements of at least two of the maintenance items in the set, the same procedural elements are combined into one procedural element in the sorted procedural elements, and
   wherein the maintenance items in the set include reaction system washing and reaction cell replacement, and at least one of the procedural elements of the reaction system washing and at least one of the procedural elements of the reaction cell replacement are combined into one procedural element in the sorted procedural elements, and
   wherein the control unit is further programmed to control the reaction system to automatically perform one or more of the sorted procedural elements of the reaction system washing and the reaction cell replacement according to the sorted order.

2. The analyzing device for clinical examinations according to claim 1,
   wherein the control unit is further programmed to:
   control the sorting unit to sort the extracted procedural elements such that, among the maintenance items in the set to be performed in a power OFF state of the analyzing device and the maintenance items in the set to be performed in a power ON state of the analyzing device, the maintenance items to be performed in the power OFF state are sorted to be performed first, as one of the rules,
   when the maintenance items include water supply tank cleaning, cleaning of the bifurcated tube filter, the reaction system washing, and the reaction cell replacement, control the sorting unit to sort the procedural elements of the water supply tank cleaning and the cleaning of the bifurcated tube which are maintenance items to be performed in the power OFF state and the procedural elements of the reaction system washing and the reaction cell replacement which are maintenance items to be performed in the power ON state so as to be performed consecutively in the order, and
   control the reaction system to automatically perform one of the sorted procedural elements of the water supply tank cleaning and the cleaning of the bifurcated tube filter according to the sorted order.

3. The analyzing device for clinical examinations according to claim 1,
   wherein the control unit is further programmed to:
   when the maintenance items in the set include at least two maintenance items for a same unit, control the sorting unit to sort the procedural elements of the at least two maintenance items for the same unit so as to be performed consecutively in the order, as one of the rules, and
   when the maintenance items in the set include washing tank cleaning, the reaction system washing, and the reaction cell replacement, control the sorting unit to sort the procedural elements of the washing tank cleaning, the reaction system washing, and the reaction cell replacement, which are the maintenance items of a reaction disk in the reaction system, so as to be performed consecutively in the order.

4. The analyzing device for clinical examinations according to claim 1,
   wherein the storage device further stores a plurality of required times for performing each of the maintenance items, and
   wherein the control unit is further programmed to calculate a time required until the maintenance to be performed is completed, and display, on the display unit, the calculated time.

5. The analyzing device for clinical examinations according to claim 1,
   wherein storage device further stores at least one of a date and a time of previous performance of each of the maintenance items or a presence or absence of an alarm at the time of previous performance of each of the maintenance items.

6. The analyzing device for clinical examinations according to claim 1, wherein the control unit is further programmed to display a description of the maintenance items in the set to be performed in the order on the display unit.

7. A management system for an analyzing device for clinical examinations comprising:
   an analyzing device including a plurality of components for clinical examinations;
   a storage device storing a plurality of maintenance items for the analyzing device, a plurality of predetermined time intervals for performing maintenance of each of the maintenance items, and a plurality of procedural elements that constitute each of the maintenance items, where two or more of the maintenance items include a same procedural element among the plural procedural elements;

an extracting unit configured to, upon reception of an instruction to perform maintenance, extract the procedural elements of a set of two or more of the maintenance items to be performed on the basis of the time intervals stored in the storage device;

a sorting unit configured to sort the extracted procedural elements of each of the maintenance items in the set in an order on the basis of predetermined rules;

a display unit configured to display the sorted procedural elements of each of the maintenance items in the set in the order sorted by the sorting unit; and a control unit programmed to control the reaction disk, the storage unit, the extracting unit and the sorting unit, wherein the control unit is further programmed to control the sorting unit to sort the extracted procedural elements based on the rules, which include:

when the same procedural elements are included in the extracted procedural elements of at least two of the maintenance items in the set, the same procedural elements are combined into one procedural element in the sorted procedural elements, wherein the maintenance items in the set include reaction system washing and reaction cell replacement, and at least one of the procedural elements of the reaction system washing and at least one of the procedural elements of the reaction cell replacement are combined into one procedural element in the sorted procedural elements, and wherein the control unit is further programmed to control the components to automatically perform one or more of the sorted procedural elements of the reaction system washing and the reaction cell replacement according to the sorted order.

8. The management system for an analyzing device for clinical examinations according to claim 7, wherein the control unit is further programmed to:

control the sorting unit to sort the extracted procedural elements such that, among the maintenance items in the set to be performed in a power OFF state of the analyzing device and the maintenance items in the set to be performed in a power ON state of the analyzing device, the maintenance items to be performed in the power OFF state are sorted to be performed first, as one of the rules, when the maintenance items in the set include water supply tank cleaning, cleaning of the bifurcated tube filter, the reaction system washing, and the reaction cell replacement, control the sorting unit to sort the procedural elements of the water supply tank cleaning and the cleaning of the bifurcated tube which are maintenance items to be performed in the power OFF state, and the procedural elements of the reaction system washing and the reaction cell replacement which are maintenance items to be performed in the power ON state so as to be performed consecutively in the order, and control the one or more components to automatically perform one of the sorted procedural elements of the water supply tank cleaning and the cleaning of the bifurcated tube filter according to the sorted order.

9. The management system for an analyzing device for clinical examinations according to claim 7, wherein the control unit is further programmed to:

when the maintenance items in the set include at least two maintenance items for a same component, control the sorting unit to sort the procedural elements of the at least two maintenance items for the same component so as to be performed consecutively in the order, as one of the rules, and when the maintenance items in the set include washing tank cleaning, the reaction system washing, and the reaction cell replacement, control the sorting unit to sort the procedural elements of the washing tank cleaning, the reaction system washing, and the reaction cell replacement, which are the maintenance items of a reaction disk in the reaction system, so as to be performed consecutively in the order.

10. A management method for an analyzing device for clinical examinations comprising:

a storage step for storing a plurality of maintenance items for the analyzing device, a plurality of predetermined time intervals for performing maintenance of each of the maintenance items, and a plurality of procedural elements that constitute each of the maintenance items, where two or more of the maintenance items include a same procedural element among the plural procedural elements;

an extracting step for extracting, upon reception of an instruction to perform maintenance, the procedural elements of a set of two or more of the maintenance items to be performed on the basis of the time intervals stored in the storage step;

a sorting step for sorting the extracted procedural elements of each of the maintenance items in the set into an order on the basis of predetermined rules;

a displaying step for displaying the sorted procedural elements of each of the maintenance items in the set in the sorted order; and a control step of controlling one or more components of the analysis device to automatically perform one or more of the sorted procedural elements of the maintenance items in the set according to the sorted order, wherein the rules include:

when the same procedural elements are included in the extracted procedural elements of at least two of the maintenance items in the set, the same procedural elements are combined into one procedural element in the sorted procedural elements, wherein the extracted maintenance items in the set include reaction system washing and reaction cell replacement, and at least one of the procedural elements of the reaction system washing and at least one of the procedural elements of the reaction cell replacement are combined into one procedural element in the sorted procedural elements, and wherein, in the control step, the one or more components of the analysis device are controlled to automatically perform one or more of the sorted procedural elements of the reaction system washing and the reaction cell replacement according to the sorted order.

11. The management method for an analyzing device for clinical examinations according to claim 10, wherein the extracted procedural elements are sorted such that, among the maintenance items in the set to be performed in a power OFF state of the analyzing device, and the maintenance items in the set to be performed in a power ON state of the analyzing device, the maintenance items to be performed in the power OFF state are sorted to be performed first, as one of the rules, and wherein, when the extracted maintenance items include water supply tank cleaning, cleaning of the bifurcated tube filter, the reaction system washing, and the reaction cell replacement, the procedural elements of the water supply tank cleaning and the cleaning of the bifurcated tube which are maintenance items to be performed in the power OFF state and the procedural elements of the reaction system washing and the reaction cell replacement which are maintenance items to be performed in the power ON state, are sorted so as to be performed consecutively in the order, and wherein, in the control step, the one or more components of the analysis device are controlled to automatically perform one of the sorted procedural elements of the water supply tank cleaning and the cleaning of the bifurcated tube filter according to the sorted order.

12. The management method for an analyzing device for clinical examinations according to claim 10, wherein, when the extracted maintenance items in the set include at least two maintenance items for a same component, the procedural elements of the at least two maintenance items for the same component are sorted so as to be performed consecutively in the order, as one of the rules, and wherein, when the extracted maintenance items include washing tank cleaning, the reaction system washing, and the reaction cell replacement, the procedural elements of the washing tank cleaning, the reaction system washing, and the reaction cell replacement, which are the maintenance items of a reaction disk as one of the components, are sorted so as to be performed consecutively in the order.

* * * * *